United States Patent
Fankhauser et al.

(10) Patent No.: US 10,519,397 B2
(45) Date of Patent: Dec. 31, 2019

(54) POWERFUL WOODY POWDERY ODORANT

(71) Applicant: Firmenich SA, Geneva (CH)

(72) Inventors: Peter Fankhauser, Meyrin (CH); Robert Moretti, Geneva (CH); Florian De Nanteuil, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 16/307,570

(22) PCT Filed: Jun. 20, 2017

(86) PCT No.: PCT/EP2017/065072
§ 371 (c)(1),
(2) Date: Dec. 6, 2018

(87) PCT Pub. No.: WO2017/220568
PCT Pub. Date: Dec. 28, 2017

(65) Prior Publication Data
US 2019/0177654 A1    Jun. 13, 2019

(30) Foreign Application Priority Data

Jun. 22, 2016 (EP) ..................... 16175671

(51) Int. Cl.
*A61K 8/18* (2006.01)
*A61Q 13/00* (2006.01)
*C11B 9/00* (2006.01)
*C07C 13/277* (2006.01)

(52) U.S. Cl.
CPC .......... *C11B 9/0038* (2013.01); *C07C 13/277* (2013.01); *C07C 2601/20* (2017.05)

(58) Field of Classification Search
None
See application file for complete search history.

(56) References Cited

U.S. PATENT DOCUMENTS 3,816,349 A * 6/1974 Hall ............ C07C 45/455
 512/8
4,393,245 A  7/1983 Hoffman et al.
4,396,670 A  8/1983 Sinclair

FOREIGN PATENT DOCUMENTS

| DE | 19848305 C1 | 5/2000 |
|----|-------------|--------|
| WO | 99/65852 A1 | 12/1999 |
| WO | 2001/041915 A1 | 6/2001 |
| WO | 2007/026271 A1 | 3/2007 |
| WO | 2012/175437 A1 | 12/2012 |
| WO | 2015/144832 A1 | 10/2015 |

OTHER PUBLICATIONS

STIC search (Year: 2019).*
Williams et al, A mild oxidation of aldehydes to alpha,beta-unsaturated aldehydes, 1980, Tetrahedron Letters vol. 21, 4417-4420 (Year: 1980).*
International Search Report and Written Opinion for international application No. PCT/EP2017/065072, dated Jul. 18, 2017.
Graefe et al., "Acylierung von cyclododecatrien-(1c, 5t, 9t)", Tetrahedron, 1970, vol. 26, issue 11, pp. 2677-2682, see English abstract.
Bône et al., "Microencapsulated Fragrances in Melamine Formaldehyde Resins", Chimia, 2011, vol. 65, n° 3, pp. 177-181.
Dietrich et al., "Amino resins microcapsules. I. Literature and patent review," Acta Polymerica, 1989, vol. 40, n° 4, pp. 243-251.
Dietrich et al., "Amino resins microcapsules. II. Preparation and morphology", Acta Polymerica, 1989, vol. 40, n° 5, pp. 325-331.
Dietrich et al., "Amino resins microcapsules. III. Release properties", Acta Polymerica, 1989, vol. 40, n° 11, pp. 683-690.
Dietrich et al., "Amino resins microcapsules. IV. Surface tension of the resins and mechanism of capsule formation", Acta Polymerica, 1990, vol. 41, n° 2, pp. 91-95.
Herrmann A, "Controlled release volatiles under mild reaction conditions: from nature to everyday products", Angew. Chem. Int. Ed., 2007, vol. 46, pp. 5836-5863.
Lee et al., "Microencapsulation of fragrant oil via in situ polymerization: effects of pH and melamine-formaldehyde molar ratio", J Microencapsulation, 2002, vol. 19(5), pp. 559-569.
Weinmann et al., "The Rupe Rearrangement: a new efficient method for large-scale synthesis of unsaturated ketones in the pilot plant", Organic Process Research & Development, 2002, vol. 6, pp. 216-219.
International Preliminary Report on Patentability for international application No. PCT/EP2017/065072, dated Jun. 8, 2018.

* cited by examiner

*Primary Examiner* — Jessica Whiteley
(74) *Attorney, Agent, or Firm* — Armstrong Teasdale LLP

(57) ABSTRACT

The present invention relates to the use as perfuming ingredient of a compound of formula (I)

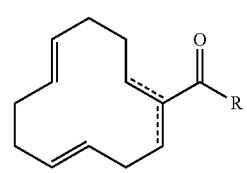

in the form of any one of its stereoisomers or a mixture thereof, and wherein one dotted line represents a carbon-carbon single bond and the other a carbon-carbon double bond; and R represents a hydrogen atom or a $C_{1-4}$ alkyl or alkenyl group; as well as to the perfuming composition and the consumer products containing said compound.

18 Claims, No Drawings

POWERFUL WOODY POWDERY ODORANT

RELATED APPLICATIONS

This application is a national stage application under 35 U.S.C. § 371 of International Patent Application PCT/EP2017/065072, filed 20 Jun. 2017, which claims the benefit of EP patent application 16175671.3, filed 22 Jun. 2016.

TECHNICAL FIELD

The present invention relates to the field of perfumery. More particularly, it concerns 1-acetyl derivatives of cyclododecatriene as defined below and their uses as perfuming ingredients. Therefore, following what is mentioned herein, the present invention comprises also the invention compound as part of a perfumed consumer product.

BACKGROUND

To the best of our knowledge, the invention's compounds, as such are known (see J. Graefe et al, in *Tetrahedron* 1970, 26, 2677,) and reported as chemical products only. Graefe does not report or suggest any organoleptic properties of the compounds of formula (I), or any use of said compounds in the field of perfumery.

To the best of our knowledge, the closest structural analogue reported as being potentially useful in the perfumery is partially hydrogenated 1-acetyl derivatives of cyclododecadiene (reported in WO 99/65852) and described as having a general woody ambery, musky odor. However, WO 99/65852 shows that the diene derivatives have moderate to poor performance in stability test and good substantivity. Nowhere is it suggested that the trienes disclosed herein can be useful perfumery ingredient with improved performances.

DESCRIPTION OF THE INVENTION

We have now surprisingly discovered that a compound of formula

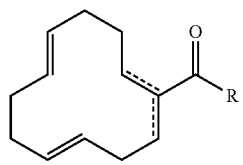
(I)

in the form of any one of its stereoisomers or a mixture thereof, and wherein one dotted line represents a carbon-carbon single bond and the other a carbon-carbon double bond; and R represents a hydrogen atom or a $C_{1-4}$ alkyl or alkenyl group;

can be used as perfuming ingredient, for instance to impart odor notes of the woody, powdery ionone type.

For the sake of clarity, by the expression "wherein one dotted line represents a carbon-carbon single bond and the other a carbon-carbon double bond", or the similar, it is meant the normal meaning understood by a person skilled in the art, i.e. that the whole bonding (solid and dotted line) between the carbon atoms connected by said dotted line, e.g. carbon 1 and 2, is a carbon-carbon single or double bond.

According to any embodiment of the invention, said compound (I) is a $C_{13}$-$C_{17}$ compound, preferably a $C_{14}$-$C_{16}$ compound.

According to any embodiment of the invention, said compound (I) is a compound of formula

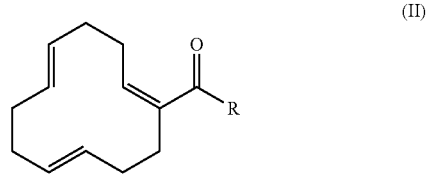
(II)

in the form of any one of its stereoisomers or a mixture thereof, and wherein R has the same meaning as in formula (I).

According to any embodiment of the invention, said compound (I) is a compound of formula

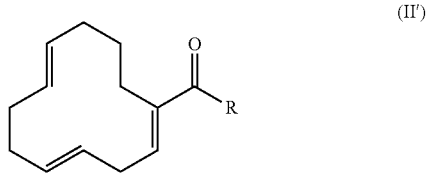
(II')

in the form of any one of its stereoisomers or a mixture thereof, and wherein R has the same meaning as in formula (I).

According to any embodiment of the invention, said invention compound is a compound wherein R represents a hydrogen atom or a $C_{1-3}$ alkyl or alkenyl group. Preferably, said invention compound is a compound wherein R represents a $C_{1-3}$ alkyl or alkenyl group. In particular, one may cite R groups such as Me, Et, $^{i}$Pr, $^{n}$Pr, prop-2-en-2-yl or cyclopropyl. Preferably, one may cite R groups such as Me, Et, $^{i}$Pr or $^{n}$Pr, prop-2-en-2yl, even more preferably Me, Et or $^{i}$Pr; even more preferably Me or Et.

For the sake of clarity, by the expression "any one of its stereoisomers", or the similar, it is meant the normal meaning understood by a person skilled in the art, i.e. that the invention compound can be any pure diastereomer (e.g. each carbon-carbon double bond is in a specific conformation E or Z).

According to any one of the above embodiments of the invention, said compound can be in the form of its E or Z isomers or of a mixture thereof, e.g. the invention comprises compositions of matter comprising, or consisting, of one or more compounds of formula (I), having the same chemical structure but differing by the configuration of the double bonds. In particular, compound (II) can be in the form of the diastereomer, e.g. (1Z,5E,9E), (1Z,5Z,9E), (1Z,5E,9Z), (1Z,5Z,9Z), (1E,5E,9E), (1E,5Z,9E), (1E,5Z,9Z), (1E,5E,9Z) or of a mixture thereof and compound (II') can be in the form of the diastereomer, e.g. (1Z,4E,8E), (1Z,4Z,8E), (1Z,4E,8Z), (1Z,4Z,8Z), (1E,4E,8E), (1E,4Z,8E), (1E,4Z,8Z), (1E,4E,8Z) or of a mixture thereof.

For the sake of clarity, one may design a mixture of diastereomers by indicating only the stereochemistry of only one carbon-carbon double bond, e.g. (1Z), it is meant the usual meaning in the art, e.g. in the case of (1Z), a mixture consisting of (1Z,5E,9E), (1Z,5Z,9E), (1Z,5E,9Z) and (1Z,5Z,9Z) diastereomers.

In particular, the invention's compound can be in the form of a mixture containing predominantly the stereoisomers (1Z,5E,9E), (1Z,5E,9Z) and (1Z,5Z,9E), the remaining being essentially the (1Z,5Z,9Z) stereoisomer. In such a case, one may define a w/w ratio (1Z,5E,9E)/[(1Z,5E,9Z)+(1Z,5Z,9E))] for such mixture of stereoisomers. According to a particular aspect of said embodiment, the compound (I) is in the form of a mixture of stereoisomers having a (1Z,5E,9E)/[(1Z,5E,9Z)+(1Z,5Z,9E))] ratio comprised between 30/70 and 1/99. Preferably, said mixture of stereoisomers has a (1Z,5E,9E)/[(1Z,5E,9Z)+(1Z,5Z,9E))] ratio comprised between 25/75 and 2/98. Even more preferably, said mixture of stereoisomers has a (1Z,5E,9E)/[(1Z,5E,9Z)+(1Z,5Z,9E))] ratio comprised between 15/85 and 2/98. Preferably, the main isomer of said mixture of stereoisomers is isomer (1Z,5E,9Z).

As specific examples of the invention's compounds, one may cite, as non-limiting example, 1-(cyclododeca-1,5,9-trien-1-yl)ethan-1-one, as obtained in Example 1 iii), in a form of a mixture of isomers (1Z,5E,9E), (1Z,5E,9Z) and (1Z,5Z,9E) with a (1Z,5E,9E)/[(1Z,5E,9Z)+(1Z,5Z,9E))] isomers ratio of 6/94 which is characterized by a woody note with cedar, vetiver, ambery aspects and which is associated with a ionone, iris, powdery note. Said compound also possesses a mossy note.

As other example, one may cite 1-((1Z,5E,9Z)-cyclododeca-1,5,9-trien-1-yl)ethan-1-one, which possesses an odor similar to the one mentioned above but distinguishing itself by not possessing a mossy note.

As other specific, but non-limiting, examples of the invention's compounds, one may cite the following ones in Table 1:

TABLE 1

Invention's compounds and their odor properties

| Compound structure and name | Odor notes |
|---|---|
| 1-(cyclododeca-1,5,9-trien-1-yl)propan-1-one | Woody and slightly ionone |
| 1-(cyclododeca-1,5,9-trien-1-yl)-2-methylpropan-1-one | Woody, cedar slightly ionone |

According to a particular embodiment of the invention, the compounds of formula (I) are 1-(cyclododeca-1,5,9-trien-1-yl)propan-1-one, 1-(cyclododeca-1,5,9-trien-1-yl)-2-methylpropan-1-one, 1-((1Z,5E,9Z)-cyclododeca-1,5,9-trien-1-yl)ethan-1-one or 1-(1Z)-cyclododeca-1,5,9-trien-1-yl)ethan-1-one.

When the odor of the invention's compounds is compared with that of the prior art diene compound, then the invention's compounds distinguish themselves by a different odor character and by having a more powerful and substantive character.

For instance comparing 1-((1Z)-cyclododeca-1,5,9-trien-1-yl)ethan-1-one with the corresponding prior art diene, the invention compound differs by having a ionone powdery note, a mossy note and by being warmer and a stronger woody character, as well as by lacking the fatty and dusty connotations of the prior art compound. Said differences lend the invention's compounds and the prior art compounds to be each suitable for different uses, i.e. to impart different organoleptic impressions.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castor oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic materials, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanol, glyoxal, glyoxylic acid or glycolaldehyde and mixtures thereof) with an amine, such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins are the ones produced by the polycondensation of an polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of H. Y. Lee et al. in Journal of Microencapsulation, 2002, vol. 19, pages 559-569, international patent publication WO 01/41915 or yet the article of S. Bône et al. in Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin or even pro-perfumes (i.e. compounds which upon degradation liberate a perfuming ingredient). Examples of pro-perfumes have been described in the literature such as in the article published by A. Herrmann in Angewandte Chemie International Edition, 2007, vol. 46, p. 5836-5863 or in more recent work of similar type, as well as in the abundant patent literature in the field.

In particular one may cite perfuming co-ingredients which are commonly used in perfume formulations, such as:
  Aldehydic ingredients: decanal, dodecanal, 2-methyl-undecanal, 10-undecenal, octanal and/or nonenal;
  Aromatic-herbal ingredients: eucalyptus oil, camphor, eucalyptol, menthol and/or alpha-pinene;
  Balsamic ingredients: coumarine, ethylvanillin and/or vanillin;
  Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
  Floral ingredients: Methyl dihydrojasmonate, linalool, Citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methylionones isomers;
  Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-Dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-Methyl-5-cyclopentadecen-1-one, 1,3,4,6,7,8-hexahydro-4,6,6,7,8,8-hexamethylcyclopenta-[G] isochromene, (1S,1'R)-2-[1-(3',3'-dimethyl-1'-cyclohexyl)ethoxy]-2-methylpropyl propanoate, and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungi or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of a perfumed consumer product comprising, as a perfuming ingredient, at least one compound of formula (I), as defined above.

The invention's compound can be added as such or as part of an invention's perfuming composition.

For the sake of clarity, by "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de perfume, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, shower or bath mousse, an oil or a gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care, a wipe, a dish detergent or a hard-surface (e.g. a floor, bath, sanitary or a windows) detergent; a leather care product; a car care product, such as a polish, a wax or a plastic cleaners.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.05% to 20% by weight, or even more, of the compounds of the invention based on the weight of the composition into which they are incorporated. In the case of perfumed consumer product, typical concentrations are in the order of 0.01% to 10% by weight, or even more, of the compounds of the invention based on the weight of the consumer product into which they are incorporated.

The invention's compounds can be prepared according to a process comprising the addition of acetylene to cyclododeca-4,8-dien-1-one, followed by the dehydration of the 1-alkynylcyclododeca-4,8-dien-1-ol obtained to form the 1-alkynylcyclododeca-1,5,9-triene which can be then transformed by hydration of the triple bond into the desired invention compounds. The dehydration and hydration steps may be performed in one pot; known as a Rupe Rearrangement, following conditions well-known by a person skilled in the art; e.g. conditions reported in DE 19848305, WO 2015/144832 or *Organic Process Research & Development* 2002, 6, 216. Consequently another aspect of the invention concerns the intermediate products of formula

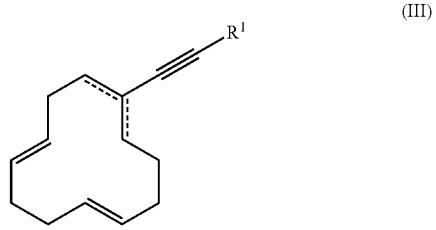

(III)

wherein the dotted lines have the same meaning as indicated above; and $R^1$ represents a hydrogen atom or a $C_{1-3}$ alkyl or alkenyl group;
and their use to produce the invention's compounds.

According to another embodiment, the invention's compounds can be prepared according to a process comprising the addition of trimethylsilanecarbonitrile to cyclododeca-4,8-dien-1-one, followed by the elimination of the (trimethylsilyl)oxy group to form a mixture of 1-cyclododeca-1,5,9-triene-1-carbonitrile and 1-cyclododeca-1,4,8-triene-1-carbonitrile which could be separated. The nitrile compound is then reduced toward the aldehyde. The addition of a Grignard reagent followed by an oxidation reaction provide the invention's compounds.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts $\delta$ are indicated in ppm with respect to TMS as standard, the coupling constants J are expressed in Hz.

Example 1

The prior art compound 1-(4,8-cyclododecadien-1-yl)-1-ethanone, could be prepared with the method reported in the prior art WO 99/65852 Example 3.
Odor: woody, cedar, fatty, dusty.

Synthesis of 1-(cyclododeca-1,5,9-trien-1-yl)ethan-1-one (Compounds of Formula (I))

i) Preparation of 1-ethynylcyclododeca-4,8-dien-1-ol (Compound A)

A THF solution of $LaCl_3 \cdot 2LiCl$ (0.6 M; 200 ml; 120 mmol) was added at room temperature to neat cyclododeca-4,8-dien-1-one (mixture of 4E,8E (5%); 4E,8Z (47%); 4Z,8E (47%) isomers, see WO 2012/175437; 70.05 g; 393 mmol). The resulting solution was cooled to 0-5° C. and treated with a THF solution of ethynyl magnesium chloride (0.5 M; 800 ml; 400 mmol) over a period of 4 hours. The resulting solution was warmed up to room temperature, at which point GC analysis indicated reaction completion. It was cooled to 0° C. and treated by slow addition of a saturated aqueous solution of ammonium chloride (200 ml). The reaction was then filtered through celite. The filtrate was extracted twice with methyl t-butyl ether. Each organic phase was washed with water and brine. Combined extracts were dried over sodium sulfate. After filtration and concentration of the filtrate, the product was purified by fractional distillation through a Fisher column to give the desired product (53.67 g; 263 mmol; 67%) with the following mixture of isomers: 6%-45%-49%.

GC-MS analysis shows the molecular ion for each isomer (M+ 204).

13C-NMR: 133.30 (d); 132.60 (d); 131.75 (d); 131.60 (d); 131.59 (d); 131.55 (d); 131.35 (d); 130.89 (d); 130.62 (d); 129.45 (d); 129.25 (d); 127.72 (d); 87.89 (s); 87.88 (s); 87.26 (s); 72.74 (d); 72.38 (s); 72.17 (s); 71.87 (d); 71.79 (d); 70.70 (s); 39.78 (t); 38.96 (t); 38.57 (t); 38.14 (t); 37.08 (t); 35.08 (t); 32.73 (t); 32.36 (t); 31.32 (t); 31.19 (t); 30.60 (t); 29.92 (t); 28.86 (t); 28.14 (t); 28.04 (t); 27.62 (t); 25.67 (t); 23.36 (t); 23.28 (t); 22.09 (t); 21.57 (t).

ii) Preparation of 1-ethynylcyclododeca-1,5,9-triene (Compound B)

42.2 g of Compound A (42.2 g; 208 mmol) was dissolved in formic acid (341 g, 7.5 mol). Water (14 g; 780 mmol) was added. After stirring for 30 minutes at room temperature, the reaction was poured onto water and extracted twice with methyl t-butyl ether. Each organic phase was washed with saturated sodium bicarbonate, water and brine. Combined extracts were dried over sodium sulfate. The residue obtained after evaporation of solvents was purified by bulb-to-bulb distillation (100° C./0.1 mbar) giving 2 fractions:

Fraction #1: 10.02 g of a 77% pure compound (isomer mixture=7%-29%-41%; 41.4 mmol)

Fraction #2: 18.24 g of a 61% pure compound (isomer mixture=5%-22%-34%; 59.7 mmol)

Total yield=101.1 mmol; 49%.

Fraction #1 was further purified by column chromatography on silica gel (eluent: heptane/ethyl acetate 99:1) followed by bulb-to-bulb distillation (100° C./0.1 mbar) to give 6.54 g (92% pure) of the desired product, as a mixture of isomers (7%-36%-49%).

GC-MS analysis shows the molecular ion for each isomer (M+ 186).

iii) Preparation of 1-(cyclododeca-1,5,9-trien-1-yl)ethan-1-one (Compound C)

AuCl (0.23 g; 0.99 mmol) was dissolved in methanol (50 ml). The above prepared Compound B (5.4 g; 29 mmol; 7%-36%-49% mixture of isomers) was added, followed by water (2.04 g; 113 mmol). The reaction was heated at reflux for 3 hours. After cooling to room temperature, it was diluted with methyl t-butyl ether. The solid was filtered off, rinsed with methyl t-butyl ether. The filtrate was concentrated. The product was purified by column chromatography on silica gel (eluent: heptane/ethyl acetate 99:1) followed by bulb-to-bulb distillation (110° C./0.2 mbar).

2.85 g of the desired product were obtained (14 mmol; 48%), as a mixture of isomers (1Z,5E,9E), (1Z,5E,9Z) and (1Z,5Z,9E) (respectively 6%-69%-25%).

GC-MS analysis shows the molecular ion for each isomer (M+204).

13C-NMR: 200.18 (s); 199.97 (s); 199.78 (s); 144.64 (d); 144.43 (d); 143.53 (d); 142.77 (s); 141.47 (s); 140.44 (s); 133.39 (d); 132.90 (d); 131.01 (d); 130.67 (d); 130.49 (d); 130.29 (d); 130.03 (d); 129.45 (d); 128.99 (d); 128.81 (d); 128.57 (d); 127.94 (d); 31.89 (t); 31.59 (t); 31.50 (t); 31.20 (t); 30.90 (t); 30.78 (t); 30.39 (t); 30.14 (t); 30.10 (t); 30.00 (t); 29.72 (t); 29.42 (t); 26.92 (t); 26.79 (t); 26.67 (t); 26.16 (t); 26.10 (q); 25.79 (q); 25.22 (t).

iv) Preparation of 1-((1Z,5E,9Z)-cyclododeca-1,5,9-trien-1-yl)ethan-1-one

Said isomer was prepared from 4Z,8E-cyclododecadienone following the step reported in example 1 point i) to iii).

13-C-NMR: 199.80 (s); 144.45 (d); 140.44 (s); 130.67 (d); 130.49 (d); 130.04 (d); 128.81 (d); 30.78 (t); 30.39 (t); 30.14 (t); 26.79 (t); 26.16 (t); 25.80 (q); 25.22 (t).

v) Preparation of 1-((1Z,5E,9E)-cyclododeca-1,5,9-trien-1-yl)ethan-1-one

Said isomer was prepared from 4E,8E-cyclododecadienone following the step reported in example 1 point i) to iii).

13-C-NMR: 200.02 (s); 144.67 (d); 141.47 (s); 133.38 (d); 132.88 (d); 129.00 (d); 128.57 (d); 31.61 (t); 31.51 (t); 31.21 (t); 30.89 (t); 30.00 (t); 26.12 (q); 25.79 (t).

vi) Carbon NMR of 1-((1Z,5Z,9E)-cyclodeca-1,5,9-triers-1-yl)ethan-1-one

13-C-NMR: 200.2, 143.5, 142.8, 131.0, 130.3, 129.4, 127.9, 30.1, 29.7, 29.4, 26.9, 26.7, 25.8, 23.7.

Example 2

Synthesis of Others Compounds of Formula (I)

i) Preparation of 1-cyclododeca-1,5,9-triene-1-carbonitrile and 1-cyclododeca-1,4,8-triene-1-carbonitrile Zinc (II) iodide (4.5 g, 14.2 mmol) and trimethylsilanecarbonitrile (20 g, 200.0 mmol) were added to 370 ml of dichloromethane. The suspension is cooled to 0° C. and cyclododeca-4,8-dien-1-one (35 g, 196 mmol, mixture of 4E,8E (5%); 4E,8Z (47%); 4Z,8E (47%) isomers, see WO 2012/175437) was added dropwise. When the addition was complete, the reaction was stirred at room temperature for 2 hours. The reaction mixture is poured over aqueous sodium bicarbonate, extracted twice with methyl tert-butyl ether, washed with water and a saturated sodium chloride solution, dried over sodium sulfate, filtered and concentrated. Bulb to bulb distillation afforded 172 mmol of a mixture of isomers of 1-((trimethylsilyl)oxy)cyclododeca-4,8-diene-1-carbonitrile.

To a mixture of 1-((trimethylsilyl)oxy)cyclododeca-4,8-diene-1-carbonitrile (172 mmol) and pyridine (150 mL) in 50 ml of toluene was added dropwise phosphoryl chloride (50 ml, 473 mmol) at room temperature. The reaction was heated at reflux for 3 hours then cooled down to room temperature. The reaction mixture was slowly poured onto ice, extracted twice with methyl tert-butyl ether, washed with 5% hydrochloric acid, aqueous sodium bicarbonate, water and a saturated sodium chloride solution, dried over sodium sulfate, filtered and concentrated. Bulb to bulb distillation afforded 40 g of crude material containing 53% of isomers of 1-cyclododeca-1,5,9-triene-1-carbonitrile and 21% of isomers of 1-cyclododeca-1,4,8-triene-1-carbonitrile. 1-cyclododeca-1,5,9-triene-1-carbonitrile (50-55° C.) and 1-cyclododeca-1,4,8-triene-1-carbonitrile (67° C.) can be separated by fractional distillation at 0.1 mbar.

ii) General Procedure GP1 for the Synthesis of Aldehyde from Nitrile Obtained in the Previous Step i)

Nitrile (87 mmol) was dissolved in 80 ml of dichloromethane and the solution was cooled to −78° C. Diisobutylaluminum hydride (120 ml, 1M in dichloromethane, 120 mmol) was added dropwise, keeping the temperature below −60° C. When addition was complete, the reaction mixture was poured slowly onto a cold 5% hydrochloric acid solution. The mixture was stirred for 16 h at room temperature, then extracted twice with methyl tert-butyl ether, washed with a saturated sodium chloride solution, dried over sodium sulfate, filtered and concentrated.

iii) General Procedure GP2 for the Synthesis of Secondary Alcohol from Aldehyde Obtained in Pervious Step ii)

Aldehyde (13.1 mmol) was dissolved in 30 ml of THF and the solution is cooled to 0° C. Alkyl magnesium bromide (15.0 ml, 1M in THF, 15.0 mmol) was added dropwise.

When addition was complete, the reaction mixture was poured slowly onto an ammonium chloride solution, then extracted twice with methyl tert-butyl ether, washed with water and a saturated sodium chloride solution, dried over sodium sulfate, filtered and concentrated.

iv) General Procedure GP3 for the Oxidation of Secondary Alcohol Obtained in Pervious Step to Ketones Alcohol (5.5 mmol) was dissolved in 15 ml of dichloromethane and the solution was cooled to 0° C. Dess-Martin periodinane (3.0 g, 7.1 mmol) was added portion wise as a solid. The reaction was stirred at room temperature for 10 minutes at which point a white precipitate had appeared. The reaction mixture was poured slowly onto a 5% sodium hydroxide solution, then extracted twice with methyl tert-butyl ether, washed with water and a saturated sodium chloride solution, dried over sodium sulfate, filtered and concentrated.

v) Characterization of Compounds Obtained Following this Procedure cyclododeca-1,5,9-triene-1-carbaldehyde cyclododeca-1,5,9-triene-1-carbaldehyde was obtained from the reduction of cyclododeca-1,5,9-triene-1-carbonitrile obtained in step i) following GP1 and send to the subsequent step without further purification.

cyclododeca-1,4,8-triene-1-carbaldehyde

Following GP1, starting from cyclododeca-1,4,8-triene-1-carbonitrile obtained in step i) (1.8 g, 9.6 mmol), cyclododeca-1,4,8-triene-1-carbaldehyde (95% pure, 410.0 mg, 2.2 mmol) was obtained as a mixture of isomers after purification by column chromatography on silica gel (eluent: heptane/ethyl acetate 99:1) and bulb-to-bulb distillation (100° C., 0.1 mbar).

GC-MS analysis shows the molecular ion for each isomer ($M^+$ 190).

$^{13}$C NMR CDCl$_3$: 196.2, 196.0, 195.8, 195.7, 195.5, 155.5, 152.5, 152.4, 150.9, 150.6, 150.2, 146.9, 145.4, 143.9, 141.3, 134.6, 133.6, 133.0, 132.5, 131.9, 131.8, 131.5, 131.3, 131.1, 131.1, 130.9, 130.7, 130.3, 130.2, 129.9, 129.8, 129.2, 128.7, 128.6, 128.5, 128.4, 128.4, 127.5, 127.1, 126.7, 126.5, 126.0, 33.3, 32.9, 32.1, 31.9, 31.8, 31.6, 31.4, 31.1, 30.7, 30.7, 30.5, 30.5, 30.4, 30.4, 30.2, 30.0, 30.0, 29.9, 29.7, 29.5, 29.4, 28.7, 28.6, 28.5, 28.5, 28.3, 28.0, 27.9, 27.9, 27.7, 27.5, 27.2, 27.1, 26.9, 26.3, 26.1, 25.9, 25.0, 24.7, 23.8, 23.5, 22.6, 22.2, 22.0, 21.6.

1-(cyclododeca-1,5,9-trien-1-yl)ethan-1-ol

Following GP2, starting from cyclododeca-1,5,9-triene-1-carbaldehyde (15.6 g, 82 mmol) and methylmagnesium bromide (60 ml, 1.4M in THF, 84 mmol), 1-(cyclododeca-1,5,9-trien-1-yl)ethan-1-ol (10 g) was obtained as a mixture of isomers after purification by bulb-to-bulb distillation (115° C., 0.1 mbar).

GC-MS analysis shows the molecular ion for each isomer ($M^+$ 206).

1-(cyclododeca-1,5,9-trien-1-yl)propan-1-ol

Following GP2, starting from cyclododeca-1,5,9-triene-1-carbaldehyde (3.0 g, 15.8 mmol) and ethylmagnesium bromide (7.9 ml, 2M in THF, 15.8 mmol), 1-(cyclododeca-1,5,9-trien-1-yl)propan-1-ol (1.7 g) was obtained as a mixture of isomers after purification by column chromatography on silica gel (eluent: heptane/ethyl acetate 99:1 to 97:3) and bulb-to-bulb distillation (130° C., 0.1 mbar).

GC-MS analysis shows the molecular ion for each isomer ($M(-H_2O)^+$ 202).

1-(cyclododeca-1,5,9-trien-1-yl)-2-methylpropan-1-ol

Following GP2, starting from cyclododeca-1,5,9-triene-1-carbaldehyde (2.5 g, 13.1 mmol) and isopropylmagnesium bromide (13.1 ml, 1M in THF, 13.1 mmol), 1-(cyclododeca-1,5,9-trien-1-yl)-2-methylpropan-1-ol (2.5 g) was obtained as a mixture of isomers after purification by column chromatography on silica gel (eluent: heptane/ethyl acetate 99:1 to 97:3) and bulb-to-bulb distillation (130° C., 0.1 mbar).

GC-MS analysis shows the molecular ion for each isomer ($M^+$ 234).

cyclododeca-1,5,9-trien-1-yl(cyclopropyl)methanol

Following GP2, starting from cyclododeca-1,5,9-triene-1-carbaldehyde (2.0 g, 10.5 mmol) and isopropylmagnesium bromide (10.0 ml, 1.26M in THF, 12.6 mmol), cyclododeca-1,5,9-trien-1-yl(cyclopropyl)methanol (1.1 g) was obtained as a mixture of isomers after purification by column chromatography on silica gel (eluent: heptane/ethyl acetate 99:1 to 97:3) and bulb-to-bulb distillation (130° C., 0.1 mbar).

GC-MS analysis shows the molecular ion for each isomer ($M^+$ 232).

1-(cyclododeca-1,4,8-trien-1-yl)ethan-1-ol

Following GP2, starting from cyclododeca-1,4,8-triene-1-carbaldehyde (2.1 g, 11.2 mmol) and methylmagnesium bromide (15 ml, 1.4M in THF, 21.0 mmol), 1-(cyclododeca-1,4,8-trien-1-yl)ethan-1-ol (1.3 g) was obtained as a mixture of isomers after bulb-to-bulb distillation (115-135° C., 0.1 mbar).

GC-MS analysis shows the molecular ion for each isomer ($M^+$ 206).

1-(cyclododeca-1,5,9-trien-1-yl)ethan-1-one

Following GP3, starting from 1-(cyclododeca-1,5,9-trien-1-yl)ethan-1-ol (2.4 g, 11.7 mmol) and Dess-Martin periodinane (5.7 g, 13.4 mmol), 1-(cyclododeca-1,5,9-trien-1-yl)ethan-1-one (0.9 g, 98% pure) was obtained as a mixture of isomers (1Z,5E,9E), (1Z,5E,9Z) and (1Z,5Z,9E) (respectively 6%-35%-57%). after purification by column chromatography on silica gel (eluent: heptane/ethyl acetate 99:1) and bulb-to-bulb distillation (100° C., 0.1 mbar).

GC-MS analysis shows the molecular ion for each isomer ($M^+$ 204).

1-(cyclododeca-1,5,9-trien-1-yl)propan-1-one

Following GP3, starting from 1-(cyclododeca-1,5,9-trien-1-yl)propan-1-ol (1.2 g, 5.5 mmol) and Dess-Martin periodinane (3.0 g, 7.1 mmol), 1-(cyclododeca-1,5,9-trien-1-yl)propan-1-one (1.0 g, 95% pure) was obtained as a mixture of isomers after bulb-to-bulb distillation (115° C., 0.1 mbar).

GC-MS analysis shows the molecular ion for each isomer ($M^+$ 218).

$^{13}$C NMR CDCl$_3$: 207.1, 206.9, 203.6, 203.4, 203.0, 202.5, 144.6, 142.7, 142.1, 141.8, 140.4, 139.7, 139.6, 138.8, 138.8, 137.8, 137.4, 137.1, 134.0, 133.4, 132.9, 132.7, 132.4, 132.0, 131.3, 131.3, 131.1, 131.1, 131.0, 130.8, 130.7, 130.4, 130.4, 130.1, 130.0, 130.0, 129.8, 129.5, 129.3, 128.8, 128.5, 128.4, 128.2, 127.9, 127.7, 127.5, 127.0, 35.5, 35.3, 34.6, 32.7, 32.5, 32.3, 32.3, 32.1, 31.8, 31.7, 31.4, 31.3, 31.0, 30.9, 30.930.8, 30.8, 30.6, 30.4, 30.4, 30.4, 30.3, 30.1, 30.0, 29.8, 29.3, 28.8, 28.7, 28.2, 28.1, 28.0, 27.9, 27.8, 27.8, 27.4, 27.2, 27.2, 26.9, 26.8, 26.7, 26.2, 25.5, 25.1, 24.7, 24.1, 23.9, 23.4, 9.1, 9.0, 9.0, 8.9, 8.0, 7.9, 7.9

1-(cyclododeca-1,5,9-trien-1-yl)-2-methylpropan-1-one

Following GP3, starting from 1-(cyclododeca-1,5,9-trien-1-yl)-2-methylpropan-1-ol (1.0 g, 4.3 mmol) and Dess-Martin periodinane (2.4 g, 5.6 mmol), 1-(cyclododeca-1,5,9-trien-1-yl)-2-methylpropan-1-one (750.0 mg, 96% pure) was obtained as a mixture of isomers after bulb-to-bulb distillation (115° C., 0.1 mbar).

GC-MS analysis shows the molecular ion for each isomer ($M^+$232).

$^{13}C$ NMR $CDCl_3$: 210.8, 207.2, 206.4, 206.0, 144.3, 142.2, 141.3, 141.2, 139.6, 139.5, 138.9, 138.4, 138.1, 137.3, 136.9, 135.5, 134.1, 133.5, 132.9, 132.6, 132.1, 131.4, 131.0, 130.9, 130.7, 130.4, 130.2, 130.1, 130.0, 129.8, 129.5, 129.1, 129.0, 128.8, 128.5, 128.4, 128.2, 128.2, 127.9, 127.6, 127.5, 127.0, 38.8, 38.5, 34.7, 34.3, 34.0, 33.9, 33.8, 33.2, 32.4, 32.1, 31.8, 31.5, 31.5, 31.4, 31.3, 30.9, 30.9, 30.8, 30.8, 30.730.4, 30.4, 30.3, 30.2, 30.1, 30.0, 29.9, 29.4, 28.8, 28.8, 28.3, 28.2, 28.0, 27.8, 27.8, 27.4, 27.0, 26.9, 26.9, 26.6, 26.1, 25.8, 25.6, 25.0, 24.6, 24.1, 23.9, 23.4, 19.8, 19.7, 19.6, 19.5, 19.3, 18.2, 18.2, 18.1 cyclododeca-1,5,9-trien-1-yl(cyclopropyl)methanone

Following GP3, starting from cyclododeca-1,5,9-trien-1-yl(cyclopropyl)methanol (0.9 g, 3.8 mmol) and Dess-Martin periodinane (1.6 g, 3.8 mmol), cyclododeca-1,5,9-trien-1-yl (cyclopropyl)methanone (400.0 mg, 75% pure) was obtained as a mixture of isomers after bulb-to-bulb distillation (110° C., 0.1 mbar).

GC-MS analysis shows the molecular ion for each isomer ($M^+$ 230).

$^{13}C$ NMR $CDCl_3$: 207.3, 207.0, 202.2, 201.7, 147.3, 142.4, 141.1, 140.9, 140.8, 138.6, 137.6, 136.4, 136.2, 133.9, 133.8, 133.3, 133.0, 132.8, 132.1, 131.9, 131.8, 131.0, 130.9, 130.6, 130.6, 130.5, 130.5, 130.4, 130.3, 130.3, 130.0, 130.0, 129.9, 129.8, 129.6, 129.5, 129.0, 128.7, 128.0, 128.0, 127.9, 127.8, 127.7, 127.0, 35.0, 34.0, 33.1, 32.5, 32.4, 32.3, 32.0, 31.9, 31.6, 31.6, 31.4, 31.1, 31.0, 30.8, 30.6, 30.5, 30.5, 30.4, 30.4, 30.2, 30.1, 30.0, 29.8, 29.2, 29.0, 28.9, 28.5, 28.4, 28.3, 28.1, 28.1, 28.0, 27.9, 27.9, 27.8, 27.6, 27.6, 27.4, 27.3, 27.1, 27.1, 26.9, 26.8, 26.6, 26.6, 26.3, 25.8, 24.7, 21.5, 21.4, 21.4, 21.2, 21.1, 21.1, 16.2, 16.0, 14.4, 14.3, 11.8, 11.8, 11.7, 10.9, 10.7, 10.7, 10.6, 4.5, 4.4, 4.2, 4.1, 3.5, 3.5, 2.9.

1-(cyclododeca-1,4,8-trien-1-yl)ethan-1-one

Following GP3, starting from 1-(cyclododeca-1,4,8-trien-1-yl)ethan-1-ol (1.0 g, 4.9 mmol) and Dess-Martin periodinane (2.7 g, 6.3 mmol), 1-(cyclododeca-1,4,8-trien-1-yl) ethan-1-one (350.0 mg, 94% pure) was obtained as a mixture of isomers after purification by column chromatography on silica gel (eluent: heptane/ethyl acetate 99:1) and bulb-to-bulb distillation (100° C., 0.1 mbar).

GC-MS analysis shows the molecular ion for each isomer ($M^+$ 204).

$^{13}C$ NMR $CDCl_3$: 200.6, 145.1, 141.0, 140.4, 139.7, 138.9, 132.9, 132.6, 131.9, 131.3, 131.0, 130.9, 130.2, 129.9, 129.4, 128.4, 128.3, 128.2, 127.9, 127.3, 126.9, 43.1, 32.5, 32.1, 31.8, 31.1, 30.9, 30.8, 30.4, 30.3, 30.2, 30.1, 29.7, 29.4, 28.7, 28.0, 27.8, 27.5, 27.3, 26.9, 26.7, 26.3, 26.1, 26.0, 25.8, 25.1, 24.7, 23.9, 23.2, 23.2, 19.6

Example 3

Preparation of a Perfuming Composition

A three perfuming compositions (A, B, C) were prepared by admixing the following ingredients:

| Ingredient | Parts by weight | | |
|---|---|---|---|
| | A | B | C |
| Geranyl acetate | 10 | 10 | 10 |
| Linalyl acetate | 200 | 200 | 200 |
| (Z)-3-Hexen-1-ol acetate | 20 | 20 | 20 |
| Styrallyl acetate | 80 | 80 | 80 |
| Ethyl acetoacetate | 40 | 40 | 40 |
| Allyl amyl glycolate | 8 | 8 | 8 |
| Ambrox ®[1] | 80 | 80 | 80 |
| Ethyl 2-methyl-pentanoate | 2 | 2 | 2 |
| Cascalone ®[2] | 40 | 40 | 40 |
| Cardamom essential oil | 40 | 40 | 40 |
| Cedar essential oil | 160 | 160 | 160 |
| Lemon essential oil | 160 | 160 | 160 |
| Coranol ®[3] | 400 | 400 | 400 |
| Allyl cyclohexylpropionate | 20 | 20 | 20 |
| Damascone alpha | 4 | 4 | 4 |
| Dihydromyrcenol | 600 | 600 | 600 |
| 2,6,10-Trimethyl-9-undecenal | 2 | 2 | 2 |
| 3-(4/2-Ethylphenyl)-2,2-dimethylpropanal | 10 | 10 | 10 |
| 2,4,6-Trimethyl-4-phenyl-1,3-dioxane | 10 | 10 | 10 |
| Galbanum essential oil | 1 | 1 | 1 |
| Habanolide ®[4] | 2000 | 2000 | 2000 |
| Helvetolide ®[5] | 200 | 200 | 200 |
| Hivernal ®[6] | 20 | 20 | 20 |
| ISO E ® Super[7] | 1600 | 1600 | 1600 |
| Lavander essential oil | 60 | 60 | 60 |
| Linalol | 200 | 200 | 200 |
| 6,6-Dimethoxy-2,5,5-trimethyl-2-hexene | 200 | 200 | 200 |
| Crystal moss | 40 | 40 | 40 |
| Hedione ®[8] | 1600 | 1600 | 1600 |
| Neobutenone ®[9] alpha | 8 | 8 | 8 |
| Dextro trans-1-(2,2,6-trimethyl-1-cyclohexyl)-3-hexanol | 80 | 80 | 80 |
| Pink pepper essential oil | 40 | 40 | 40 |
| Orange essential oil | 200 | 200 | 200 |
| Sclareolate ®[10] | 200 | 200 | 200 |
| 2-Ethyl-4,4-dimethylcyclohexanone | 4 | 4 | 4 |
| Vanilline | 20 | 20 | 20 |
| Verdox ®[11] | 80 | 80 | 80 |
| Beta ionone | 20 | 20 | 20 |
| Z 11[12] | 40 | 40 | 40 |
| 2,4-Dimethyl-3-cyclohexene-1-carbaldehyde | 4 | 4 | 4 |
| Dipropylene glycol | 1497 | 897 | 897 |
| 1-((1Z)-cyclododeca-1,5,9-trien-1-yl)ethan-1-one | 0 | 600 | 0 |
| 1-(4,8-cyclododecadien-1-yl)-1-ethanone | 0 | 0 | 600 |
| TOTAL | 10000 | 10000 | 10000 |

[1] (−)-(8R)-8,12-epoxy-13,14,15,16-tetranorlabdane[a]
[2] 7-Isopropyl-2h,4h-1,5-benzodioxepin-3-one[a]
[3] 4-cyclohexyl-2-methyl-2-butanol[a]
[4] pentadecenolide[a]
[5] (1S,1'R)-2-[1-(3',3'-dimethyl-11-cyclohexyl)ethoxy]-2-methylpropyl propanoate[a]
[6] 3-(3,3/1,1-dimethyl-5-indanyl)propanal[a]
[7] 1-(octahydro-2,3,8,8-tetramethyl-2-naphtalenyl)-1-ethanone[b]
[8] Methyl dihydrojasmonate[a]
[9] 1-(5,5-dimethyl-1-cyclohexen-1-yl)-4-penten-1-one[a]
[10] Propyl (S)-2-(1,1-dimethylpropoxy)propanoate[a]
[11] 2-tert-butyl-1-cyclohexyl acetate[b]
[12] (+)-8alpha,13:13,20-diepoxy-15,16-dinorlabdane[a]
[a] origin: Firmenich SA, Geneva, Switzerland
[b] origin: International Flavors & Fragrances, USA The presence of 1-((1Z)-cyclododeca-1,5,9-trien-1-yl) ethan-1-one in perfume B) transformed perfume A) by strongly enhancing the initial woody-cedar and powdery/ violet character as well as by adding a ambery warmness without losing freshness on the top notes. The substantively of the woody, ambery and powdery notes of perfume B) were also enhanced compared to perfume A).

The presence of 1-(4,8-cyclododecadien-1-yl)-1-ethanone in perfume C) transformed perfume A) into a weaker and much less fresh fragrance by providing fatty and dusty notes. The substantively of the woody, ambery and powdery notes are of A) was also harmed.

Overall, perfume B), when compared to perfume C), was stronger, much more woody-cedar, more powdery, warmer and not fatty and dusty. The substantivity of the woody, ambery and powdery notes was also significantly enhanced. Overall the composition was stronger at all stages.

The invention claimed is:
1. A perfuming composition comprising
i) at least one compound of formula (I)

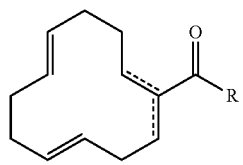

in the form of any one of its stereoisomers or a mixture thereof, and wherein one dotted line represents a carbon-carbon single bond and the other a carbon-carbon double bond; and R represents a hydrogen atom, a $C_{1-4}$ alkyl group or a $C_{1-4}$ alkenyl group;
ii) at least one ingredient selected from the group consisting of a perfumery carrier and a perfumery base; and
iii) optionally at least one perfumery adjuvant.
2. A perfumed consumer product comprising
a) at least one compound of formula (I)

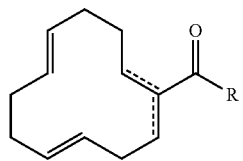

in the form of any one of its stereoisomers or a mixture thereof, and wherein one dotted line represents a carbon-carbon single bond and the other a carbon-carbon double bond; and R represents a hydrogen atom, a $C_{1-4}$ alkyl group or a $C_{1-4}$ alkenyl group or
b) a perfuming composition comprising
i) at least one compound of formula (I),

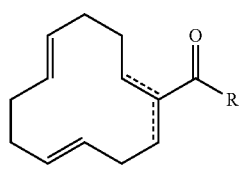

in the form of any one of its stereoisomers or a mixture thereof, and wherein one dotted line represents a carbon-carbon single bond and the other a carbon-carbon double bond; and R represents a hydrogen atom, a $C_{1-4}$ alkyl group or a $C_{1-4}$ alkenyl group;
ii) at least one ingredient selected from the group consisting of a perfumery carrier and a perfumery base; and
iii) optionally at least one perfumery adjuvant.
3. The perfumed consumer product according to claim 2, characterized in that the perfumery consumer product is a perfume, a fabric care product, a body-care product, a cosmetic preparation, a skin-care product, an air care product or a home care product.
4. The perfumed consumer product according to claim 2, characterized in that the perfumery consumer product is a fine perfume, a splash or eau de perfume, a cologne, an shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product or a car care product.
5. A compound of formula

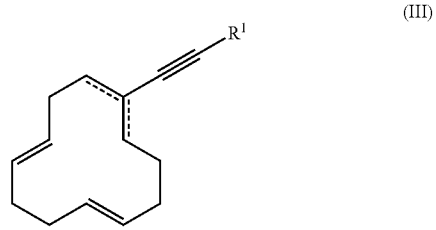

wherein one dotted line represents a carbon-carbon single bond and the other a carbon-carbon double bond; and $R^1$ represents a hydrogen atom, a $C_{1-3}$ alkyl group or a $C_{1-3}$ alkenyl group.
6. A method to confer, enhance, improve or modify the odor properties of a perfuming composition or of a perfumed article, which method comprises adding to said composition or article an effective amount of at least a compound of formula (I),

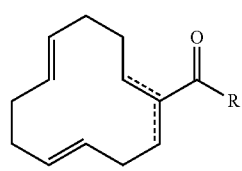

in the form of any one of its stereoisomers or a mixture thereof, and wherein one dotted line represents a carbon-carbon single bond and the other a carbon-carbon double bond; and R represents a hydrogen atom, a $C_{1-4}$ alkyl group or a $C_{1-4}$ alkenyl group.

7. The method according to claim 6, characterized in that said compound is of formula

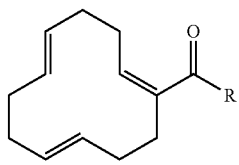

(II)

in the form of any one of its stereoisomers or a mixture thereof, and wherein R represents a hydrogen atom, a $C_{1-4}$ alkyl group or a $C_{1-4}$ alkenyl group.

8. The method according to claim 6, characterized in that R represents a Me, Et, i-Pr, n-Pr or prop-2-ene-2yl group.

9. The method according to claim 6, characterized in that R represents a Me or Et group.

10. The method according to claim 6, characterized in that said compound is 1-((1Z)-cyclododeca-1,5,9-trien-1-yl)ethan-1-one.

11. The perfuming composition according to claim 1, characterized in that said compound is of formula

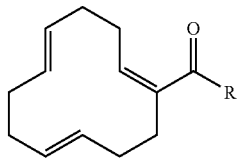

(II)

in the form of any one of its stereoisomers or a mixture thereof, and wherein R has the same meaning as in claim 1.

12. The perfuming composition according to claim 1, characterized in that R represents a Me, Et, i-Pr, n-Pr or prop-2-ene-2yl group.

13. The perfuming composition according to claim 1, characterized in that R represents a Me or Et group.

14. The perfuming composition according to claim 1, characterized in that said compound is 1-((1Z)-cyclododeca-1,5,9-trien-1-yl)ethan-1-one.

15. The perfumed consumer product according to claim 2, characterized in that said compound is of formula

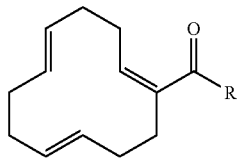

(II)

in the form of any one of its stereoisomers or a mixture thereof, and wherein R has the same meaning as in claim 2.

16. The perfumed consumer product according to claim 2, characterized in that R represents a Me, Et, i-Pr, n-Pr or prop-2-ene-2yl group.

17. The perfumed consumer product according to claim 2, characterized in that R represents a Me or Et group.

18. The perfumed consumer product according to claim 2, characterized in that said compound is 1-((1Z)-cyclododeca-1,5,9-trien-1-yl)ethan-1-one.

* * * * *